United States Patent [19]
Cheng et al.

[11] Patent Number: 5,600,048
[45] Date of Patent: Feb. 4, 1997

[54] CONTINUOUS PROCESS FOR PREPARING ETHYLBENZENE USING LIQUID PHASE ALKYLATION AND VAPOR PHASE TRANSALKYLATION

[75] Inventors: Jane C. Cheng, Clarksburg; C. Morris Smith; Chaya R. Venkat, both of Princeton, all of N.J.; Dennis E. Walsh, Richboro, Pa.

[73] Assignee: Mobil Oil Corporation, Fairfax, Va.

[21] Appl. No.: 364,145

[22] Filed: Dec. 27, 1994

[51] Int. Cl.$^6$ ................................................. C07C 2/66
[52] U.S. Cl. ........................... 585/449; 585/467; 585/453
[58] Field of Search ...................... 585/467, 474, 585/453, 449

[56] References Cited

U.S. PATENT DOCUMENTS

| | | | |
|---|---|---|---|
| 3,751,504 | 8/1973 | Keown et al. | 585/323 |
| 3,914,383 | 10/1975 | Kirsch et al. | 423/328 |
| 4,016,218 | 4/1977 | Haag et al. | 260/671 R |
| 4,070,407 | 1/1978 | Haag et al. | 260/671 R |
| 4,136,128 | 1/1979 | Haag et al. | 260/671 R |
| 4,169,111 | 9/1979 | Wight | 585/323 |
| 4,288,646 | 9/1981 | Olah | 585/458 |
| 4,459,426 | 7/1984 | Inwood et al. | 585/323 |
| 4,547,605 | 10/1985 | Kresge et al. | 585/467 |
| 4,555,311 | 11/1985 | Ward | 203/21 |
| 4,774,377 | 9/1988 | Barger et al. | 585/466 |
| 4,857,666 | 8/1989 | Barger et al. | 585/474 |
| 4,870,222 | 9/1989 | Bakas et al. | 585/323 |
| 4,885,426 | 12/1989 | Chu et al. | 585/474 |
| 4,891,458 | 1/1990 | Innes et al. | 585/323 |
| 5,081,323 | 1/1992 | Innes et al. | 585/467 |
| 5,118,894 | 6/1992 | Le | 585/446 |
| 5,149,894 | 9/1992 | Holtermann et al. | 585/467 |
| 5,157,185 | 10/1992 | Chu et al. | 585/467 |
| 5,227,558 | 7/1993 | Shamshourm et al. | 585/446 |
| 5,334,795 | 8/1994 | Chu et al. | 585/467 |
| 5,371,310 | 12/1994 | Bennett et al. | 585/467 |

*Primary Examiner*—Glenn A. Caldarola
*Attorney, Agent, or Firm*—Ronald A. Bleeker; Peter W. Roberts

[57] ABSTRACT

There is provided a process for preparing ethylbenzene using liquid phase alkylation and vapor phase transalkylation. The liquid phase alkylation reaction may be catalyzed by an acidic solid oxide, such as MCM-22, MCM-49 and MCM-56. The vapor phase transalkylation may be catalyzed by a medium-pore size zeolite such as ZSM-5. The process may be run continuously with the continuous introduction of fresh benzene feed containing at least 500 ppm of nonbenzene hydrocarbon impurities. The combined ethylbenzene product of these alkylation and transalkylation reactions has very low levels of impurities including xylene, hydrocarbons having 7 or less carbon atoms and hydrocarbons having 9 or more carbon atoms.

24 Claims, 2 Drawing Sheets

FIG. 1

FIG. 2

CONTINUOUS PROCESS FOR PREPARING ETHYLBENZENE USING LIQUID PHASE ALKYLATION AND VAPOR PHASE TRANSALKYLATION

BACKGROUND

There is provided a process for preparing ethylbenzene using liquid phase alkylation and vapor phase transalkylation.

Ethylbenzene is a valuable commodity chemical which is currently used on a large scale industrially for the production of styrene monomer. Ethylbenzene may be produced 0 by a number of different chemical processes but one process which has achieved a significant degree of commercial success is the vapor phase alkylation of benzene with ethylene in the presence of a solid, acidic ZSM-5 zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° to 900° F. (315° to 480° C.), but are usually maintained above about 700° F.(about 370° C.) in order to keep the content of the more highly alkylated benzenes such as diethylbenzene at an acceptably low level. Pressures typically vary from atmospheric to 3000 psig (about 20785 kPa abs) with a molar ratio of benzene to ethylene from about 1:1 to 25:1, usually about 5:1 (benzene:ethylene). Space velocity in the reaction is high, usually in the range of 1 to 6, typically 2 to 5, WHSV based on the ethylene flow, with the benzene space velocity varying accordingly, in proportion to the ratio of the reactants. The products of the reaction include ethylbenzene which is obtained in increasing proportions as temperature increases together with various polyethylbenzenes, principally diethylbenzene (DIEB) which also are produced in increasing amounts as reaction temperature increases. Under favorable operating conditions on the industrial scale, an ethylene conversion in excess of 99.8 weight percent may be obtained at the start of the cycle.

In the commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level. This commercial process is known as the Mobil/Badger process and is described in more detail in an article by Francis G. Dwyer, entitled "Mobil/Badger Ethylbenzene Process-Chemistry and Catalytic Implications", appearing on pages 39–50 of a book entitled *Catalysis of Organic Reactions*, edited by William R. Moser, Marcel Dekker, Inc., 1981.

Ethylbenzene production processes are described in U.S. Pat. Nos. 3,751,504 (Keown), 4,547,605 (Kresge), and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pat. Nos. 4,169,11 (Wight) and 4,459,426 (Inwood), in both of which a preference for large-pore size zeolites such as zeolite Y is expressed, Ln distinction to the intermediate-pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

Ethylbenzene (EB) can be synthesized from benzene and ethylene ($C_2=$) over a variety of zeolitic catalysts in either the liquid phase or in the vapor phase. An advantage of a liquid phase process is its low operating temperature and the resulting low content of by-products.

U.S. Pat. No. 4,891,458 describes the liquid phase synthesis of ethylbenzene with zeolite Beta.

U.S. Pat. No. 5,149,894 describes the liquid phase synthesis of ethylbenzene with a crystalline aluminosilicate material designated SSZ-25.

U.S. Pat. No. 5,334,795 describes the liquid phase synthesis of ethylbenzene with a crystalline aluminosilicate material designated MCM-22.

SUMMARY

There is provided a process for preparing ethylbenzene, said process comprising the steps of:

(a) contacting benzene and ethylene with a solid oxide catalyst in a liquid phase alkylation reaction zone under sufficient liquid phase conditions to generate ethylbenzene product and byproducts comprising diethylbenzene; and (b) contacting said diethylbenzene byproduct from step (a) and benzene with a solid oxide catalyst in a vapor phase transalkylation reaction zone under sufficient vapor phase conditions to generate an effluent comprising another ethylbenzene product, wherein benzene feed which is introduced into said vapor phase transalkylation zone of step (b) comprises nonbenzene hydrocarbons having from 5 to 7 carbon atoms, and wherein said nonbenzene hydrocarbons having from 5 to 7 carbon atoms are converted to hydrocarbons having a different boiling point in said transalkylation zone, and wherein unreacted benzene is recycled in said alkylation zone and in said transalkylation zone.

There is also provided a continuous process for preparing ethylbenzene, said process comprising the steps of:

(a) introducing benzene, benzene coboilers, and ethylene into a liquid phase alkylation reaction zone, wherein said benzene and said ethylene are reacted in the presence of an alkylation catalyst under sufficient liquid phase conditions to generate an effluent comprising ethylbenzene product, unreacted benzene, unreacted benzene coboilers, and byproducts comprising diethylbenzene and butylbenzene, said alkylation catalyst comprising an acidic solid oxide selected from the group consisting of MCM-22, MCM-49 and MCM-56;

(b) passing the effluent from said liquid phase alkylation reaction zone of step (a) to a separation zone, wherein said effluent is separated into separate streams comprising (i) a light stream comprising benzene and benzene coboilers, (ii) an intermediate product stream, and (iii) a heavy stream comprising diethylbenzene and butylbenzene;

(c) passing said heavy stream (iii) from step (b) along with benzene and benzene coboilers to a vapor phase transalkylation reaction zone, wherein said benzene and diethylbenzene are reacted in the presence of a transalkylation catalyst under sufficient vapor phase conditions to generate an effluent comprising another ethylbenzene product and unreacted benzene, said transalkylation catalyst comprising a medium-pore size zeolite;

(d) passing the effluent from said vapor phase transalkylation reaction zone to the separation zone of step (b), wherein said effluent is separated into separate streams comprising (i) a light stream comprising unreacted benzene, (ii) an intermediate product stream, and (iii) a heavy stream comprising unreacted diethylbenzene;

(e) recycling unreacted benzene along with benzene coboilers recovered in separation steps (b) and (d) in a closed recycle loop to said alkylation reactor of step (a) and to said transalkylation reactor of step (c);

(f) introducing fresh benzene feed into said benzene recycle loop at a rate sufficient to make up for benzene converted in said alkylation zone and in said transalkylation zone, wherein said fresh benzene comprises impurities comprising benzene coboiling nonbenzene hydrocarbons having from 5 to 7 carbon atoms, said benzene coboiling hydrocarbons being at least partially converted to hydrocarbons having a different boiling point in said transalkylation zone of step (c), and butylbenzene being at least partially converted to one or more different hydrocarbons in said transalkylation zone of step (c); and (g) recovering an ethylbenzene product from the intermediate product stream of steps (b) and (d), the recovered ethylbenzene product comprising less than 200 ppm xylene, less than 100 ppm of hydrocarbons having 7 or less carbon atoms and less than 100 ppm of hydrocarbons having 9 or more carbon atoms.

EMBODIMENTS

Current commercial processes for preparing ethylbenzene (EB) conduct both alkylation and transalkylation steps in the same phase, i.e., either both steps in the vapor phase or both steps in the liquid phase. In the vapor phase commercial process, higher temperatures are required to maintain vapor phase conditions. At the temperatures employed in these vapor phase conditions, considerable quantities of xylene impurities are formed. Since the boiling point for xylenes is very close to the boiling point for ethylbenzene, the ethylbenzene product from such an all vapor phase process exceeds 700 ppm of xylene impurities. Earlier versions of the previously mentioned Mobil/Badger process may produce an ethylbenzene product having 1200–1600 ppm of xylene impurities. These xylene impurities, which coboil with ethylbenzene, may contaminate downstream products derived from ethylbenzene, such as styrene and polystyrene.

The lower operating temperature required for the all liquid phase process produces less than 100 ppm xylene byproducts, but it has now been discovered that certain feed impurities in the form of benzene coboilers, when present in the benzene feed, will tend to accumulate in the all liquid phase system over time. It has further been discovered that certain alkylation byproducts, particularly $C_3$-benzenes and $C_4$-benzenes, tend to accumulate over time in the all liquid phase system.

Less expensive sources of benzene, which are practicable for use as fresh feedstocks to the present process, have considerable levels of impurities. These impurities are difficult to separate from benzene by distillation, because they have boiling points close to the boiling point of benzene. These difficultly separable impurities are referred to herein as benzene coboilers. These benzene coboilers include hydrocarbons having from 5 to 7 carbon atoms. These hydrocarbon impurities include cycloaliphatic, paraffinic, olefinic and aromatic compounds. Particularly problematic benzene coboilers include cyclohexane and methylcyclopentane. Toluene is another particular example of a benzene coboiler which may be present. Altogether, these benzene coboilers may be present in 500–700 ppm levels in benzene sources suitable for use as fresh feeds to the present process.

These benzene coboilers are largely inert under the lower temperature liquid phase conditions. Expensive separation procedures are required to satisfactorily remove these coboilers from benzene. However, if these coboilers are not removed, they will build up in the system, because as benzene is reacted in the system it must be replaced by fresh feed and each introduction of fresh feed introduces more inert benzene coboilers to the all liquid phase system.

In addition to the problem of benzene coboiler build-up caused by continuous introduction of these impurities along with fresh benzene feed, a net production of such coboilers can be realized in the all liquid phase process as a result of ethylene oligomerization reactions in the liquid phase alkylation reactor. More particularly, ethylene may trimerize to form hexene, which, in turn may undergo cyclization reactions to form cyclohexane and/or methylcyclopentane. Ethylene oligomerization reactions in the alkylation reactor can also be the root cause of the generation of other problematic impurities in the all liquid phase system. These impurities comprise $C_9$ and $C_{10}$ aromatics, especially propylbenzene and butylbenzene. Butylbenzene may be formed in the alkylation reactor when ethylene first dimerizes to form butene, which, in turn, alkylates benzene. Each ethylene trimer (i.e., hexene) can also exist in an equilibrium state with 2 molecules of propylene, which, in turn, can also alkylate benzene to form propylbenzene.

The $C_9$ and $C_{10}$ aromatic impurities tend to build-up primarily in the polyethylbenzene recycle loop to the transalkylation reactor of the all liquid phase system. However, when these impurities are generated in sufficient levels they can permeate the entire system. In the all liquid phase system, the primary route for removal of the $C_9$ and $C_{10}$ aromatic impurities is by further alkylation or transalkylation with ethyl groups, followed by rejection from the system as heavies. These side reactions result in a net consumption of ethylene and can reduce overall liquid yields by up to 2%.

As a result of the build-up of impurities in the all liquid phase system, these impurities tend to be carried over into the recovered ethylbenzene product. More particularly, in a typical all liquid phase system, the ethylbenzene product obtained from the all liquid phase system may contain about 600 ppm of benzene coboilers and about 800 ppm of $C_9$ and $C_{10}$ aromatics.

All vapor phase processes, such as the Mobil/Badger process, produce an ethylbenzene product which contains little or no (e.g., less than 50 ppm) benzene coboilers and $C_9$ and $C_{10}$ aromatics. Under the high temperature operating conditions of the all vapor phase process, benzene coboilers and $C_9$ and $C_{10}$ aromatics are cracked and rejected as lights. However, as mentioned previously, the ethylbenzene product from the all vapor phase system will contain at least 700 ppm of xylene impurities. In summary, a typical ethylbenzene product from an all vapor phase system will contain at least 700 ppm xylene, no benzene coboilers and no $C_9$ and $C_{10}$ aromatics, whereas a typical ethylbenzene product from an all liquid phase system will contain at less than 100 ppm xylene, 600 ppm benzene coboilers and 800 ppm $C_9$ and $C_{10}$ aromatics.

The present liquid phase alkylation/vapor phase transalkylation system achieves low levels of all of these impurities (i.e., xylene, benzene coboilers and $C_9$ and $C_{10}$ aromatics) in the ethylbenzene product without the need for prohibitively expensive separation schemes. The separators employed in the present system may be comparable in scale to those employed in the Mobil/Badger all vapor phase system.

In the present liquid-vapor phase process, alkylation takes place at low temperatures in the liquid phase, thereby generating little or no xylene. In the vapor phase transalkylation reaction, propylbenzene, butylbenzene and benzene coboilers are converted to hydrocarbons having different boiling points by a variety of reactions, including cracking, dealkylation, alkylation (e.g., with cracked fragments), and transalkylation. Benzene generated by these reactions is recycled, whereas other conversion products are rejected from the system as lights or heavies. Only a small amount of xylene is produced in the transalkylation reaction.

The recovered ethylbenzene product from the present system may have less than 200 ppm xylene, less than 100 ppm of hydrocarbons having 7 or less carbon atoms and less than 100 ppm of hydrocarbons having 9 or more carbon atoms.

The fresh benzene feed for the present system may contain considerable amounts of impurities in the form of benzene coboilers. More particularly, elemental analysis of the benzene feed may reveal the presence of at least 500 ppm of nonbenzene hydrocarbons having from 5 to 7 carbon atoms.

The present alkylation and transalkylation reaction take place in separate zones. Each of these zones may comprise a single reactor or more than one reactor connected in series. Preferably, these zones are each encompassed within a single alkylation reactor and a single transalkylation reactor.

The catalyst used in the present process comprises at least one acidic solid oxide. Examples of such acidic solid oxides include aluminosilicates and materials, such as SAPO's, which contain oxides of elements other than silicon and aluminum. These acidic solid oxides may be amorphous or crystalline materials. The crystalline materials may have non-layered, 3-dimensional framework structures, or layered structures, such as the layered structures of clays. Preferred acidic solid oxides are zeolites, particularly medium-pore size and large-pore size zeolites.

The catalyst for the present liquid phase alkylation reaction may comprise a medium- or large-pore size zeolite. Particular examples of acidic solid oxides which may be use to catalyze the alkylation reaction include MCM-22, MCM-36, MCM-49, MCM-56, zeolite Beta, zeolite X, zeolite Y, and mordenite. Of these crystalline materials, MCM-22, MCM-49 and MCM-56 are particularly preferred.

The catalyst for the present vapor phase transalkylation reaction may comprise a medium- or large-pore size zeolite. Particular examples of acidic solid oxides which may be use to catalyze the transalkylation reaction include MCM-22, ZSM-5, ZSM-11, ZSM-12, ZSM-22, ZSM-23, ZSM-35, ZSM-48 and ZSM-50. Of these crystalline materials, ZSM-5 is particularly preferred.

A convenient measure of the extent to which a zeolite provides control of access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g., less than 5 Angstroms. On the other hand, zeolites which provide relatively free access to the internal zeolite structure have a low value for the Constraint Index, and usually pores of large size, e.g., greater than 8 Angstroms. The method by which Constraint Index is determined is described fully in U.S. Pat. No. 4,016,218, incorporated herein by reference for details of the method.

A zeolite which may be used in the present reaction may be a medium- or large-pore size zeolite. This zeolite may have a Constraint Index of 12 or less. Zeolites having a Constraint Index of 2–12 are generally regarded to be medium-pore size zeolites. Zeolites having a Constraint Index of less than 1 are generally regarded to be large-pore size zeolites. Zeolites having a Constraint Index of 1–2 may be regarded as either medium- or large-pore size zeolites.

The members of the class of medium-pore size zeolites may have an effective pore size of generally from about 5 to about 8 Angstroms, such as to freely sorb normal hexane. In addition, the structures provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the medium-pore size type. Windows of 10-membered rings are preferred, although, in some instances, excessive puckering of the rings or pore blockage may render these zeolites ineffective.

Although 12-membered rings in theory would not offer sufficient constraint to constitute a medium-size pore, it is noted that the puckered 12-ring structure of TMA offretite does show some constrained access. Other 12-ring structures may exist which may be regarded to be medium-pore sized, and therefore, it is not the present intention to classify a particular zeolite solely from theoretical structural considerations.

Constraint Index (CI) values for some typical materials are:

|  | CI (at test temperature) | |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |

| CI (at test temperature) | | |
|---|---|---|
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Mordenite | 0.5 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y (Deal Y) | 0.5 | (510° C.) |
| Erionite | 38 | (316° C.) |
| Zeolite Beta | 0.6–2.0 | (316° C.–399° C.) |

The above-described Constraint Index provides a definition of those zeolites which are particularly useful in the present process. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood by those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein of 12 or less.

Examples of zeolites having a Constraint Index of from 1 to 12 include ZSM-5, ZSM-11, ZSM-12, ZSM-22, ZSM-23, ZSM-35, ZSM-38, and ZSM-48.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in greater detail in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. Pat. No. 4,556,477, the entire contents of which is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,406,859. The description of that zeolite, and particularly the specified X-ray diffraction pattern thereof, is incorporated herein by reference.

ZSM-48 is more particularly described in U.S. Pat. No. 4,234,231, the entire contents of which is incorporated herein by reference.

The large-pore zeolites, including those zeolites having a Constraint Index less than 2, are well known to the art and have a pore size sufficiently large to admit the vast majority of components normally found in a feed chargestock. The zeolites are generally stated to have a pore size in excess of 7 Angstroms and are represented by zeolites having the structure of, e.g., Zeolite Beta, Zeolite Y, Ultrastable Y (USY), Dealuminized Y (Deal Y), Mordenite, ZSM-3, ZSM-4, ZSM-18, and ZSM-20. A crystalline silicate zeolite well known in the art and useful in the present invention is faujasite. The ZSM-20 zeolite resembles faujasite in certain aspects of structure, but has a notably higher silica/alumina ratio than faujasite, as does Deal Y.

Although zeolite Beta has a Constraint Index less than 2, it is to be noted that it does not have the same structure as the other large-pore zeolites, nor does it behave exactly like a large-pore zeolite. However, zeolite Beta is a particularly preferred zeolite for use in the present reaction.

Zeolite ZSM-14 is described in U.S. Pat. No. 3,923,636, to which reference is made for details of this catalyst.

Zeolite ZSM-20 is described in U.S. Pat. No. 3,972,983, to which reference is made for details of this catalyst. L5 Zeolite Beta is described in U.S. Pat. Nos. 3,308,069, and Re. No. 28,341, to which reference is made for details of this catalyst.

Low sodium Ultrastable Y molecular sieve (USY) is described in U.S. Pat. Nos. 3,293,192 and 3,449,070, to which reference is made for details of this catalyst.

Dealuminized Y zeolite (Deal Y) may be prepared by the method found in U.S. Pat. No. 3,442,795, to which reference is made for details of this catalyst.

Zeolite UHP-Y is described in U.S. Pat. No. 4,401,556, to which reference is made for details of this catalyst.

A particular acidic solid oxide, which may be use to catalyze either the present liquid phase alkylation reaction or the present vapor phase transalkylation reaction, is MCM-36. MCM-36 is a pillared layered material having zeolitic layers. For the purposes of the present disclosure, MCM-36 shall be considered to be a zeolite. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36.

As mentioned hereinabove, MCM-22, MCM-49 and MCM-56 are particularly preferred acidic solid oxides for catalyzing the present liquid phase alkylation reaction. These crystalline oxides may also be used to catalyze the present vapor phase transalkylation reaction. MCM-22 and its use to catalyze the synthesis of alkylaromatics, including ethylbenzene, is described in U.S. Pat. Nos. 4,992,606;

5,077,445; and 5,334,795. MCM-49 is described in U.S. Pat. No. 5,236,575. The use of MCM-49 to catalyze the synthesis of alkylaromatics, including ethylbenzene, is described in copending U.S. application Ser. Nos. 08/078,368 and 08/078,369, each filed Jun. 16, 1993. MCM-56 is described in copending U.S. application Ser. No. 08/051,952, filed Apr. 26, 1993. The use of MCM-56 to catalyze the synthesis of alkylaromatics including ethylbenzene is described in copending U.S. application Ser. No. 08/249,609, filed May 26, 1994. MCM-56 is believed to be a layered material with zeolitic layers. For the purposes of the present disclosure, MCM-56 shall be considered to be a zeolite.

MCM-56 is a unique layered material having a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g., from about 5 to less than about 25, usually from about 10 to less than about 20, more usually from about 13 to about 18. In the as-synthesized form, the material has a formula, on an anhydrous basis and in terms of moles of oxides per n moles of $YO_2$, as follows:

$$(0-2)M_2O: (1-2)R:X_2O_3:(n)YO_2$$

wherein M is an alkali or alkaline earth metal, and R is an organic moiety. The M and R components are associated with the material as a result of their presence during synthesis, and are easily removed by post-synthesis methods hereinafter more particularly described.

The MCM-56 material may be thermally treated and in the calcined form exhibits high surface area (greater than 300 m²/gm) and unusually large sorption capacity for certain large molecules when compared to previously described materials such as calcined PSH-3, SSZ-25, MCM-22, and MCM-49. The MCM-56 wet cake, i.e., as-synthesized MCM-56, is swellable indicating the absence of interlayer bridges, in contrast with MCM-49 which is unswellable.

To the extent desired, the original alkali or alkaline earth, e.g., sodium, cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

The MCM-56 material appears to be essentially pure with little or no detectable impurity crystal or layer phases and has an X-ray diffraction pattern which is distinguished by the combination of line positions and intensities from the patterns of other known as-synthesized or thermally treated materials as shown below in Table I (as synthesized) and Table II (calcined). In these tables, intensities are defined relative to the d-spacing line at 12.4 Angstroms.

TABLE I

| MCM-56 | | Closest Relative Layered Material | | Closest Relative 3-Dimensional Material MCM-49 | |
|---|---|---|---|---|---|
| Interplanar d-Spacing (A) | Relative Intensity | Interplanar d-Spacing (A) | Relative Intensity | Interplanar d-spacing (A) | Relative Intensity |
| — | — | 13.5 | m | — | — |
| 12.4 ± 0.2 | vs | 12.4 | m–vs | 12.5 | vs |
| — | — | 11.1 | m | 11.2 | m–s |
| 9.9 ± 0.3 | m | — | — | — | — |
| — | — | 9.2 | m | 9.0 | m |
| 6.9 ± 0.1 | w | 6.9 | w | 6.9 | w |
| 6.4 ± 0.3 | w | 6.7 | w | 6.4 | w |
| 6.2 ± 0.1 | w | 6.2 | w | 6.2 | m |
| 3.57 ± 0.07 | m–s | 3.56 | w–m | 3.55 | w–m |
| 3.44 ± 0.07 | vs | 3.43 | s–vs | 3.44 | vs |

TABLE II

| MCM-56 | | MCM-22 | | MCM-49 | |
|---|---|---|---|---|---|
| Interplanar d-Spacing (A) | Relative Intensity | Interplanar d-Spacing (A) | Relative Intensity | Interplanar d-spacing (A) | Relative Intensity |
| 12.4 ± 0.2 | vs | 12.4 | m–vs | 12.4 | vs |
| — | — | 11.0 | m–s | 11.1 | s |
| 9.9 ± 0.3 | m–s | — | — | — | — |
| — | — | 8.8 | m–vs | 8.9 | m–s |
| 6.9 ± 0.1 | w | 6.9 | w–m | 6.9 | w |
| 6.2 ± 0.1 | s | 6.2 | m–vs | 6.2 | m |
| 3.55 ± 0.07 | m–s | 3.56 | w–m | 3.57 | w |
| 3.42 ± 0.07 | vs | 3.42 | vs | 3.43 | s–vs |

The materials used for generation of the data in Table I were wet cake layered MCM-56, wet cake layered material synthesized with the same organic directing agent which, when calcined, transforms into MCM-22, and wet cake crystalline MCM-49. The materials used for the data in Table II were the calcined materials used for Table I. Calcination of each material was in air at 540° C. for 2–20 hours. The most effective diagnostic feature allowing the initial differentiation between MCM-56 and the other members of this family (MCM-22 and MCM-49-type materials) is observed in the region of 8.8–11.2 Angstroms d-spacing. The latter species exhibit two resolved maxima at approximately 8.8–9.2 Angstroms and 10.8–11.2 Angstroms with a distinct depression between them. MCM-56 is characterized by a broad band centered around d-spacing 9.9 Angstroms. While the band may have asymmetric profile, for example with an inflection point, the emergence of a depression may be indicative of the onset of MCM-49 formation and the loss of MCM-56.

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar the relative intensities of the lines, $I/I_o$ is one-hundredth spacings, d's, were calculated in Angstrom units (A), and of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-56 with similar materials, e.g., MCM-49, MCM-22, and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members (e.g., compare middle columns of Tables I and II). An examination of the X-ray diffraction patterns of both precursor and calcined forms shows a number of reflections with very similar position and intensity, while other peaks are different. Some of these differences are directly related to the changes in the axial dimension and bonding.

Crystalline MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and 6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. The ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak.

Other features which collectively distinguish MCM-56 from the similar materials described above are summarized in Table III below.

TABLE III

| Feature | MCM-22 | MCM-49 | MCM-56 |
|---|---|---|---|
| As-synthesized: | | | |
| Structure | layered | 3-dimensional | layered |
| Swellable | yes | no | yes |
| Condenses upon Calcination | yes | yes | no |
| Calcined: | | | |
| Sorption capacity for 1,3,5-tri- | low | low | high |

TABLE III-continued

| Feature | MCM-22 | MCM-49 | MCM-56 |
|---|---|---|---|
| methyl benzene[1] | | | |
| Initial uptake of 2,2-di-methylbutane[2] | slow | slow | fast |

[1]Low sorption capacity is defined as less than about 8 to 10 μl/g. High capacity is at least about 4 times the low capacity. Calcined MCM-56 sorbs at least about 35 μl/g.
[2]Initial uptake is defined as time to adsorb the first 15 mg of 2,2-dimethylbutane/gram of sorbent. Fast uptake is less than 20 seconds; slow uptake is at least 5 times the fast value.
One gram of calcined MCM-56 sorbs 15 mg of 2,2-dimethylbutanes in less than about 20 seconds, e.g., less than about 15 seconds.

The acidic solid oxide crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the process of this invention. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the solid crystal, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The alkylation reaction is carried out in the liquid phase. Suitable conditions can be selected by reference to the phase diagram for benzene.

In the liquid phase, the reaction is carried out with the benzene feedstock in the liquid phase with the reaction conditions (temperature, pressure) appropriate to this end.

Liquid phase operation may be carried out at temperatures between 300° and 552° F. (about 150° to 289°c.), usually in the range of 400° to 500° F. (about 205° to 260° C.).

Pressures during the alkylation step may be as high as about 3000 psig, (about 20875 kPa abs.) and generally will not exceed 1000 psig (about 7000 kPa). The reaction may be carried out in the absence of hydrogen and accordingly the prevailing pressures are those of the reactant species. In a high pressure liquid phase operation, the temperature may be from about 300° to 552° f. (about 149° C. to 289° C.) with the pressure in the range of about 400 to 800 psig. The space velocity may be from about 0.1 to 20 WHSV, based on the ethylene feed, although lower space velocities are preferred for the liquid phase reaction, for example, from about 0.5 to about 3 WHSV, e.g., from about 0.75 to 2.0 WHSV (ethylene). The ratio of the benzene to the ethylene in the alkylation reactor may be from 1:1 to 30:1 molar, normally about 5:1 to 20:1 and in most cases from about 5:1 to 10:1 molar.

The alkylation process can be carried out as a continuous operation utilizing a fixed, fluidized or moving bed catalyst system.

Particular conditions for carrying out the liquid phase alkylation step may include a temperature of from about 150° C. to about 260° C., a pressure of 7000 kPa or less, a WHSV based on ethylene of from about 0.5 to about 2.0 $hr^{-1}$, and a mole ratio of benzene to ethylene of from 1:1 to 30:1.

The vapor phase transalkylation step may be carried out at a temperature of from about 260° C. to about 482° C., a pressure of from about 50 to 500 psig, a WHSV based on the weight of the total vapor feed to the reaction zone of from about 1 to about 50 $hr^{-1}$, and a mole ratio of benzene to diethylbenzene of from about 1 to 50.

The benzene feed to the transalkylation reactor may comprise at least 100 ppm, e.g., at least 200 ppm, of benzene coboilers, especially in the form of nonbenzene hydrocarbons having from 5 to 7 carbon atoms per molecule.

In the present vapor phase transalkylation step, ethylbenzene is believed to be produced by an actual transalkylation reaction involving both benzene and polyethylbenzenes (e.g., diethylbenzene) as reactants. However, it is also possible that at least some ethylbenzene is generated by straight dealkylation of polyethylbenzenes during this step.

When conducting alkylation, various types of reactors can be used. Large scale industrial processes may employ a fixed-bed reactor operating in an upflow or downflow mode or a moving-bed reactor operating with concurrent or countercurrent catalyst and hydrocarbon flows. These reactors may contain a single catalyst bed or multiple beds and may be equipped for the interstage addition of ethylene and interstage cooling. Interstage ethylene addition and more nearly isothermal operation enhance product quality and catalyst life. A moving-bed reactor makes possible the continuous removal of spent catalyst for regeneration and replacement by fresh or regenerated catalysts.

In a particular embodiment of the present invention, the alkylation process is carried out with addition of ethylene in at least two stages. Preferably, there will be two or more catalyst beds or reactors in series, wherein at least a portion of the ethylene is added between the catalyst beds or reactors. Interstage cooling can be accomplished by the use of a cooling coil or heat exchanger. Alternatively, interstage cooling can be effected by staged addition of the benzene feedstock in at least two stages. In this instance, at least a portion of the benzene feedstock is added between the catalyst beds or reactors, in similar fashion to the staged addition of ethylene described above. The staged addition of benzene feedstock provides additional cooling to compensate for the heat of reaction.

In a fixed-bed reactor or moving-bed reactor, alkylation is completed in a relatively short reaction zone following the introduction of ethylene. Ten to thirty percent of the reacting benzene molecules may be alkylated more than once. Transalkylation is a slower reaction which occurs in the alkylation zone. If transalkylation proceeds to equilibrium, better than 90 wt.% selectivity to monoalkylated product is generally achieved. Thus, transalkylation increases the yield of monoalkylated product by reacting the polyalkylated products with additional benzene.

The alkylation reactor effluent contains the excess benzene feed, monoalkylated product, polyalkylated products, and various impurities. The benzene feed is recovered by distillation and recycled to the alkylation and transalkylation reactors. A small bleed may be taken from the recycle stream if needed to eliminate unreactive impurities from the loop. However, since benzene coboilers are eliminated via the present vapor phase transalkylation step, this bleeding process is substantially less needed than in an all liquid phase alkylation/transalkylation process. Since little or no benzene needs to be bled out of the present benzene recycle loop, benzene can be essentially recycled to extinction in the present process.

The percentage of ethylene converted in the liquid phase alkylation step may be at least 95%, e g., at least 97%. The weight ratio of ethylbenzene to diethylbenzene produced in the liquid phase alkylation step may be from about 2 to about 30.

When MCM-22, MCM-49 or MCM-56 is chosen as the acidic solid oxide to catalyze the present liquid phase alkylation reaction, the reaction is highly selective for the production of ethylbenzene. More particularly, this alkylation product may comprise at least 92 wt % of ethylbenzene, with less than 7 wt % of diethylbenzene and less than 1 wt %, e.g., less than 0.5 wt %, of triethylbenzene. In the present liquid phase alkylation step, MCM-22, MCM-49 and MCM-56 are believed to be substantially more active than zeolite Y. Therefore, the MCM-22, MCM-49 or MCM-56 catalyzed reaction requires less catalyst and a smaller alkylator for a given level of throughput than a zeolite Y catalyzed reaction. Furthermore, at the end of a reaction cycle, the catalyst containing MCM-22, MCM-49 or MCM-56 can be regenerated in situ in the alkylation reactor, whereas other catalysts may require removal from the reactor for regeneration, due to the large catalyst inventory and possible local overheat during the regeneration process.

The medium-pore size zeolites, especially ZSM-5, used in the present vapor phase transalkylation step, are more shape selective than large-pore size zeolites, such as USY, used as catalysts for liquid phase transalkylations. Consequently, the present vapor phase transalkylation step, catalyzed by medium-pore size zeolites, produces less heavies (e.g., $C_{11}+$ hydrocarbons) than liquid phase transalkylations catalyzed with large- pore size zeolites.

The present liquid-vapor phase reaction system may comprise one or more separation zones situated downstream from the reaction zones. Preferably, the products from both the liquid phase alkylation zone and the vapor phase transalkylation zone are passed into a single separation zone. This separation zone may comprise a series of three distillation columns. In a first distillation column, the products from the alkylation zone and the transalkylation zone are introduced as a feed and benzene is recovered as an overhead stream. The recovered benzene overhead stream is recycled as a reactant to both the liquid phase alkylation zone and the vapor phase transalkylation zone. The bottoms from the first distillation column are passed as a feed to a second distillation column. Ethylbenzene product is recovered as an overhead stream, and the bottoms from the second distillation column are passed as a feed stream to a third distillation column. Diethylbenzenes and triethylbenzenes are recovered as an overhead stream from the third distillation column, and this stream comprising diethylbenzene is passed as a reactant stream to the transalkylation zone. The bottoms from the third distillation column are rejected from the system as heavies.

The separation zone for the present liquid-vapor phase system may be essentially the same as those illustrated in the art for all liquid phase or all vapor phase systems. Such a separation zone for an all liquid phase system is illustrated in U.S. Pat. No. 4,169,111, and such a separation zone for an all vapor phase is illustrated in FIG. 3 on page 45 of the article by Francis G. Dwyer, entitled "Mobil/Badger Ethylbenzene Process-Chemistry and Catalytic Implications", appearing on pages 39–50 of a book entitled *Catalysis of Organic Reactions*, edited by William R. Moser, Marcel Dekker, Inc., 1981.

Fresh benzene feed is preferably introduced into the present system directly into the separation zone or at a point immediately upstream from the separation zone. When fresh benzene is introduced into the system in this manner, the benzene, which is introduced into both the liquid phase alkylation zone and the vapor phase transalkylation zone, is essentially a mixture of recycled benzene and fresh fed benzene.

EXAMPLE 1

2.0 g of an MCM-22 catalyst (~4 cc 1/16" extrudate, sized to 1/16' length, 35% alumina binder, 620 alpha value, 25 $SiO_2/Al_2O_3$) was mixed with ~20 cc of 20–40 mesh quartz chips, and then charged to an isothermal, down-flow, fixed-bed reactor. The catalyst was dried at 125° C. and 1 atm with 50 cc/min of flowing $N_2$ for 2 hours. $N_2$ was turned off. Benzene was fed into the reactor at 16.7 WHSV for 1 hour and then at 8.35 WHSV while the reactor temperature and pressure were increased to 150° C. and 500 psig, respectively. After the desired temperature and pressure were reached, ethylene was introduced from a mass flow controller at 0.55 WHSV (5.5 benzene/ethylene molar ratio). After lining out, liquid products were collected in a cold-trap and analyzed off-line with a Varian 3700 GC. Offgas was analyzed with an on-line Carle refinery gas analyzer. Ethylene conversion was determined by measuring unreacted ethylene in the offgas relative to feed ethylene. Total material balances were 100±2%. During the 18 day experiment, the effects of temperature (200°–320° C.), ethylene WHSV (1.1 to 2.2 $h^{-1}$) and benzene/ethylene molar ratio (4.5–6.5) were studied all at 500 psig. The catalyst activity and selectivity for liquid phase ethylbenzene synthesis are compared with those of MCM-49, MCM-56, and zeolite Beta in Example 7. At the end of the run, no activity loss was observed.

EXAMPLE 2

4.0 g of the same MCM-22 catalyst (~8 cc, mixed with ~16 cc of 20–40 mesh quartz chips) was used for this run also at 500 psig. The reaction was brought on stream similarly to what was described in Example 1. The initial conditions were 182° C., 0.55 ethylene WHSV, and 5.5 benzene/ethylene molar ratio. Ethylene conversion decreased from 94 to 82% over 5 days at 182° C. Increasing reactor temperature did not yield stable ethylene conversion until ~210° C. At 220°C., the ethylene conversion stabilized at 97–98% for 18 days without aging. Liquid products obtained at 220° C. and 97–98% ethylene conversion were nearly identical to what was observed from Example 1 at similar conditions.

EXAMPLE 3

Although no aging was observed at 220° C. in Example 2, the catalyst was subjected to a regeneration procedure at the end of the stability study to assess its robustness. The catalyst was regenerated in situ at 1 atm in a mixture of air and $N_2$ (total flow of 200 cc/min): 25% of air for 30 minutes at 400° C.; 50%, 75% and 100% of air for 30 minutes each at 450° C.; then 100% air at 538° C. for 2 hours. The temperature was decreased to 220° C. The regenerated catalyst was then tested for 5 days under conditions identical to those before regeneration: 220° C., 500 psig, 0.55 ethylene WHSV, and 5.5 benzene/ethylene molar ratio. The regenerated catalyst was slightly more active reaching 98–99% ethylene conversion (97–98% before regeneration). The DEB/EB molar ratio also increased slightly after regeneration from 0.05 to 0.07.

EXAMPLE 4

2.0 g of an MCM-49 catalyst (~4 cc 1/16" extrudate, sized to 1/16' length, 35% alumina binder, 910 alpha value, 18 $SiO_2/Al_2O_3$, mixed with 20 cc of 20–40 mesh quartz chips) was tested similarly to what was described for MCM-22 in Example 1. Benzene was fed into the reactor at 30 WHSV for 1 hour and then at 16.7 WHSV while the reactor temperature and pressure were increased to 220° C. and 500 psig, respectively. After reaching 220° C. and 500 psig, ethylene was introduced at 1.1 WHSV (5.5 benzene/ethylene molar ratio). During the 25 day experiment, the effects of temperature (200°–320° C.), ethylene WHSV (1.1 to 2.2 $h^{-1}$) and benzene/ethylene molar ratio (4.5–6.5) were studied all at 500 psig. The catalyst activity and selectivity for liquid phase ethylbenzene synthesis are compared with those of MCM-22, MCM-56, and zeolite Beta in Example 7. At the end of the run, the catalyst was tested again at conditions identical to those used at the beginning of the run. No activity loss was observed.

EXAMPLE 5

1.0 g of an MCM-56 catalyst (2 cc 1/16" extrudate, sized to 1/16", 35% alumina binder, 400 alpha value, 18 $SiO_2/Al_2O_3$, mixed with ~10 cc of 20–40 mesh quartz chips) was tested similarly to what was described for MCM-22 in Example 1. Benzene was fed into the reactor at 45 WHSV for 1 hour and then at 16.7 WHSV while the reactor temperature and pressure were increased to 220° C. and 500 psig, respectively. After reaching 220° C. and 500 psig, ethylene was introduced at 1.1 WHSV (5.5 benzene/ethylene molar ratio). During the 13 day experiment, the effects of temperature (200°–320° C.) and ethylene WHSV (1.1 to 2.8 $h^{-1}$) were studied at 500 psig and ~5.5 benzene/ethylene molar ratio. The catalyst activity and selectivity for liquid phase ethylbenzene synthesis are compared with those of MCM-22, MCM-49, and zeolite Beta in Example 7. At the end of the run, the catalyst was tested again at conditions identical to those used at the beginning of the run. No activity loss was observed.

EXAMPLE 6

2.0 g of a zeolite-Beta catalyst (~4 cc 1/16" extrudate, sized to 1/16" length, 35% alumina binder, 690 alpha value, 43 $SiO_2/Al_2O_3$, mixed with 20 cc of 20–40 mesh quartz chips) was tested similarly to what was described for MCM-22 in Example 1. Benzene was fed into the reactor at 30 WHSV for 1 hour and then at 25 WHSV while the reactor temperature and pressure were increased to 160° C. and 500 psig, respectively. After reaching 160° C. and 500 psig, ethylene was introduced at 1.65 WHSV (5.5 benzene/ethylene molar ratio). At 160° C., ethylene conversion declined from 97 to 74% in 4 days and continued to decline thereafter. Increasing temperature to 180° C. did not recover catalyst activity. The catalyst was air regenerated using procedures described in Example 3 and was brought on stream again at 220° C., 500 psig, 1.65 ethylene WHSV, and 5.5 benzene/ ethylene molar ratio. The catalyst was then tested under various conditions to study the effects of temperature (180–320° C.), ethylene WHSV (1.1 to 3.3 h$^{-1}$), and benzene/ethylene molar ratio (4.5–6.5) at 500 psig. Stable and 97+% ethylene conversion was achieved at 180° C., 1.1 ethylene WHSV, and 5.5 benzene/ethylene molar ratio. The catalyst activity and selectivity for liquid phase ethylbenzene synthesis are compared with those of MCM-22, MCM-49, and MCM-56 in Example 7. At the end of the run, the catalyst was tested again at conditions identical to those used at the beginning of the run. No activity loss was observed.

EXAMPLE 7

Figure 1:
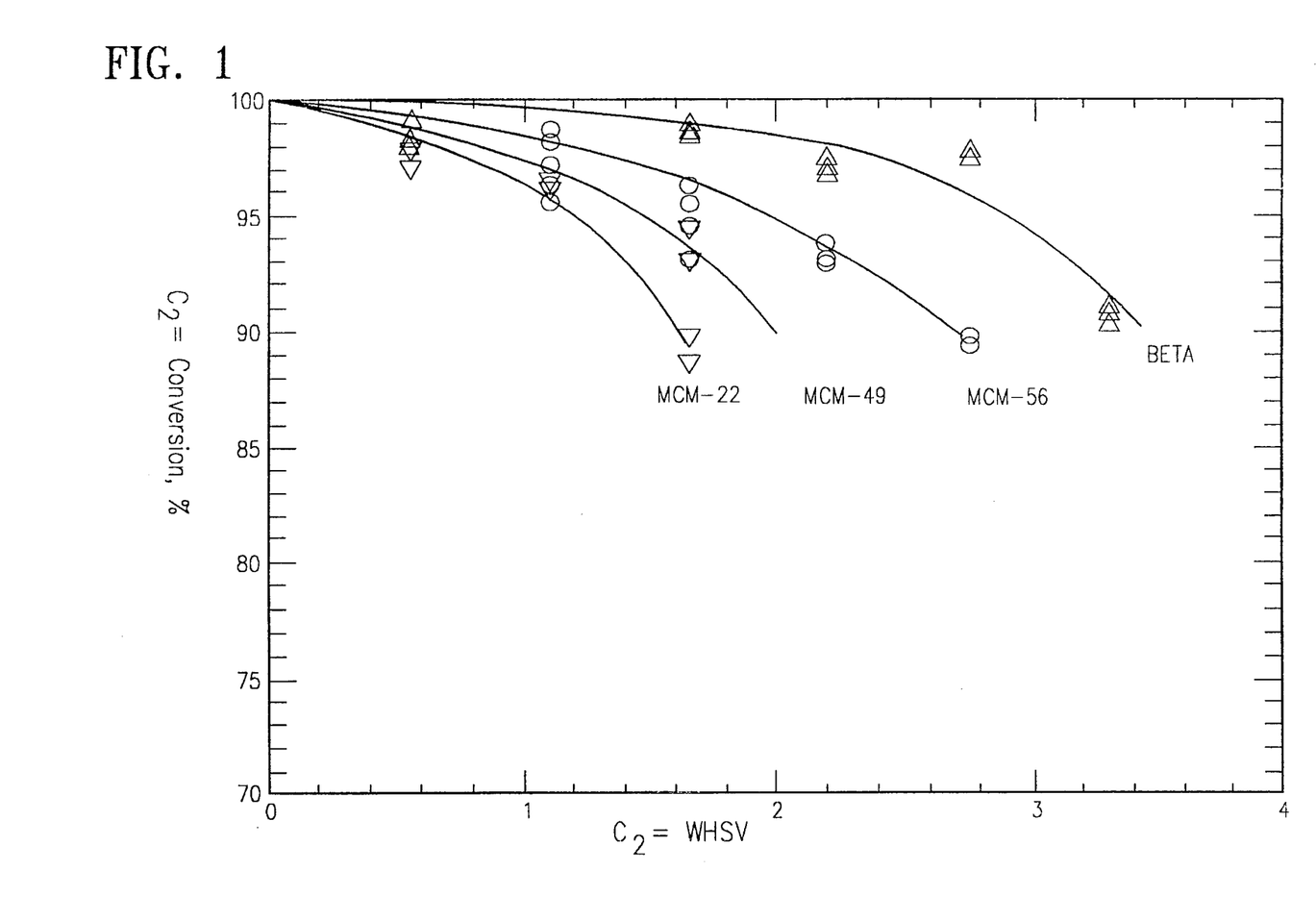
FIG. 1 is a graph showing a comparison of the activity of MCM-22, MCM-49, MCM-56 and zeolite Beta for catalyzing the liquid phase synthesis of ethylbenzene.

FIG. 1 compares catalyst activity at 220° C., 500 psig, and 5.5 benzene/ethylene molar ratio. At constant ethylene conversion (e.g., 95%), the relative catalyst activity is: MCM-22: MCM-49: MCM-56: zeolite Beta=1.0:1.2:1.6:2.2

Table 1 indicates that at 96+% C$_2$=conversion, MCM-22, MCM-49, and MCM-56's overall alkylation selectivities to EB and polyethylbenzene (99.9 mol %) are all higher than that of zeolite Beta. The EB selectivities of MCM-22, MCM-49, and MCM-56 (93–95 mol %) are 5–7 mol % higher than zeolite Beta. MCM-22, MCM-49, and MCM-56 made less polyethylbenzene and less non-EB by-products than zeolite Beta.

TABLE 1

Ethylbenzene Synthesis - Selectivity Comparison

| Catalyst/ 35% Al$_2$O$_3$ | MCM-22 | MCM-49 | MCM-56 | Zeolite Beta |
|---|---|---|---|---|
| C$_2$=WHSV | 1.1 | 1.1 | 1.65 | 2.2 |
| C$_2$=Conversion, % | 96.6 | 97.1 | 96.2 | 97.0 |
| Product distr. (mol %) | | | | |
| EB | 94.0 | 95.3 | 93.7 | 88.0 |
| DEB | 5.7 | 4.5 | 6.0 | 10.6 |
| TEB+ | 0.2 | 0.1 | 0.2 | 1.1 |
| Σ | 99.9 | 99.9 | 99.9 | 99.7 |
| xylenes | 0.00 | 0.00 | 0.00 | 0.00 |
| n-C$_3$-Bz + cumene | 0.00 | 0.00 | 0.00 | 0.00 |
| sec-C$_4$-Bz | 0.07 | 0.06 | 0.04 | 0.13 |
| other C$_9$+ aromatics | 0.02 | 0.02 | 0.02 | 0.14 |
| Σ (by products) | 0.09 | 0.09 | 0.06 | 0.27 |

220° C., 500 psig, and 5.5 benzene/C$_2$ = molar ratio

Figure 2:
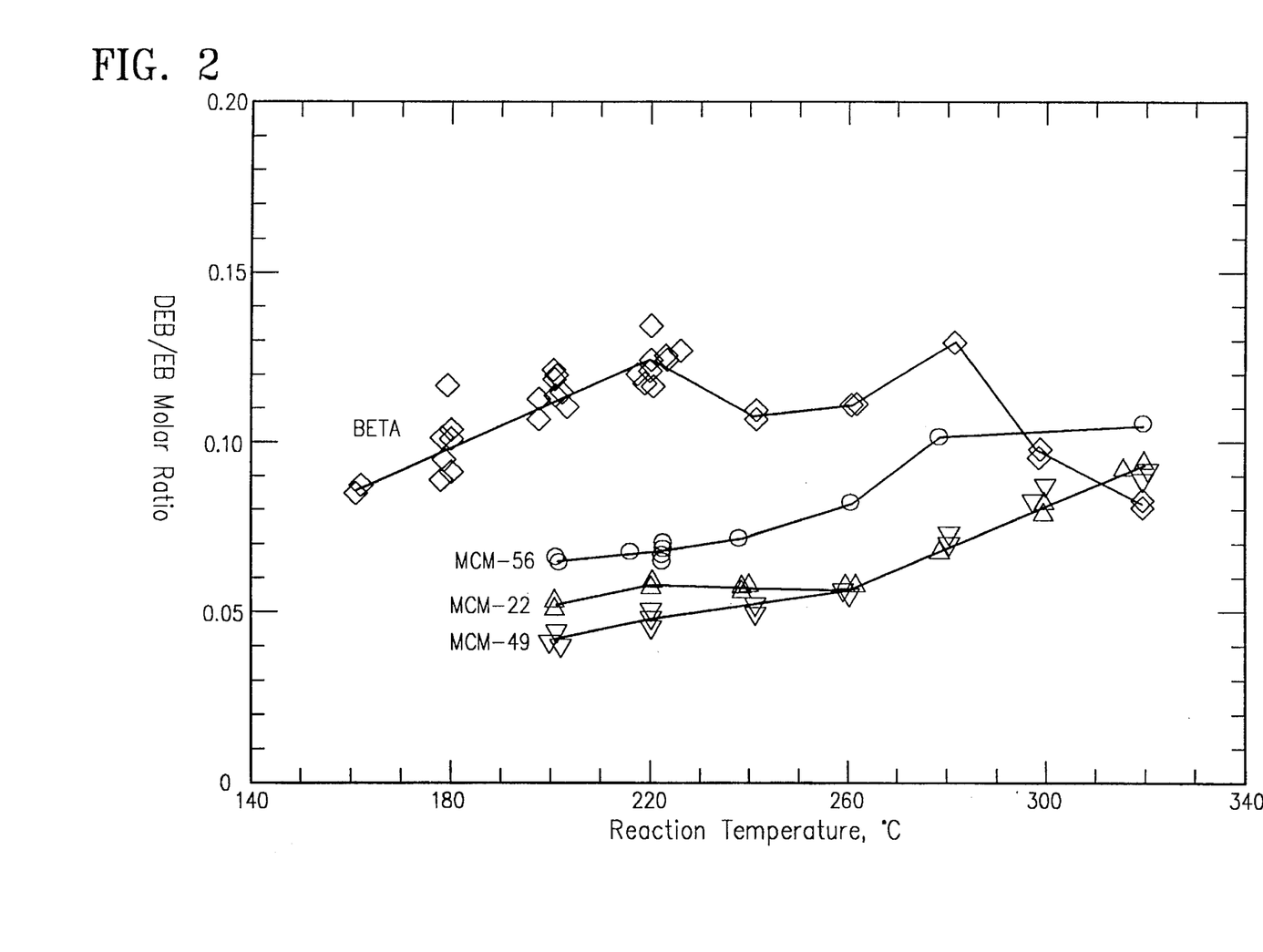
FIG. 2 is a graph showing a comparison of the selectivity of MCM-22, MCM-49, MCM-56 and zeolite Beta for catalyzing the liquid phase synthesis of ethylbenzene.

Catalyst selectivities (further represented as DEB/EB molar ratio) at other temperatures are compared in FIG. 2. In the liquid phase (<260° C. at 500 psig), MCM-22, MCM-49, and MCM-56 catalysts made less DEB than zeolite Beta. At 20° C., MCM-22, MCM-49, and MCM-56 made ~50% less DEB than zeolite Beta.

EXAMPLE 8

After distillation, the polyethylbenzene (PEB) rich bottoms product is mixed with benzene (recovered by a prior distillation step) and processed in the transalkylation reactor in the vapor phase over a medium pore zeolite such as ZSM-5. Transalkylation conditions are typically 635°– 662° F., 120 psig, 40 total WHSV (benzene and PEB), and benzene/PEB weight ratio. Under these conditions, conversion per pass is ≧45%. The products are sent to distillation section for benzene and incremental EB recovery, and PEB is recycled to the transalkylator. The resultant EB quality from the overall process is excellent (<200 ppm xylenes, no benzene coboilers, and no C$_9$ and C$_{10}$ aromatics).

What is claimed is:

1. A process for preparing ethylbenzene, said process comprising the steps of:

(a) contacting benzene and ethylene with an acidic solid oxide catalyst in a liquid phase alkylation reaction zone under sufficient liquid phase conditions to generate ethylbenzene product and byproducts comprising diethylbenzene; and (b) contacting said diethylbenzene byproduct from step (a) and benzene with an acidic solid oxide catalyst in a vapor phase transalkylation reaction zone under sufficient vapor phase conditions to generate an effluent comprising another ethylbenzene product, wherein benzene feed which is introduced into said vapor phase transalkylation zone of step (b) comprises nonbenzene hydrocarbons having from 5 to 7 carbon atoms, and wherein nonbenzene hydrocarbons having from 5 to 7 carbon atoms are converted to hydrocarbons having a different boiling point in said transalkylation zone, and wherein unreacted benzene is recycled in said alkylation zone and in said transalkylation zone.

2. A process according to claim 1, wherein said benzene feed to said vapor phase transalkylation zone comprises at least 100 ppm of said nonbenzene hydrocarbons having from 5 to 7 carbon atoms, and wherein the temperature in said liquid phase alkylation reaction zone of step (a) is lower than the temperature of said vapor phase transalkylation zone of step (b).

3. A process according to claim 1, wherein said benzene feed to said vapor phase transalkylation zone comprises at least 200 ppm of said nonbenzene hydrocarbons having from 5 to 7 carbon atoms.

4. A process according to claim 1, wherein the alkylation step (a) comprises contacting said benzene and ethylene with a catalyst comprising a large-pore size zeolite, and wherein said nonbenzene hydrocarbons having from 5 to 7 carbon atoms, which are converted to different hydrocarbons having a different boiling point in said transalkylation zone, are largely inert in said alkylation zone.

5. A process according to claim 1, wherein the alkylation step (a) comprises contacting said benzene and ethylene with a catalyst comprising a solid crystalline aluminosilicate selected from the group consisting of MCM-22, MCM-36, MCM-49, MCM-56, zeolite Beta, zeolite X, zeolite Y and mordenite.

6. A process according to claim 1, wherein the alkylation step (a) comprises contacting said benzene and ethylene with a catalyst comprising a solid crystalline aluminosilicate selected from the group consisting of MCM-22, MCM-49, and MCM-56.

7. A process according to claim 1, wherein the transalkylation step (b) comprises contacting said benzene and diethylbenzene with a catalyst comprising a medium- pore size zeolite.

8. A process according to claim 1, wherein the transalkylation step (b) comprises contacting said benzene and diethylbenzene with a catalyst comprising a solid crystalline aluminosilicate selected from the group consisting of MCM-22, ZSM-5, ZSM-11, ZSM-12, ZSM-22, ZSM-23, ZSM-35, ZSM-48 and ZSM-50.

9. A process according to claim 1, wherein the transalkylation step (b) comprises contacting said benzene and diethylbenzene with a catalyst comprising ZSM-5.

10. A process according to claim 1, wherein the molar ratio of benzene to ethylene in the liquid phase alkylation step (a) is greater than or equal to 1 and wherein the percentage of ethylene converted in step (a) is at least 95%.

11. A process according to claim 10, wherein the percentage of ethylene converted in step (a) is at least 97%.

12. A process according to claim 1, wherein the weight ratio of ethylbenzene to diethylbenzene produced in liquid phase alkylation step (a) is from about 2 to about 30.

13. A process according to claim 1, wherein the liquid phase alkylation step (a) is carried out at a temperature of from about 150° C. to about 260° C., a pressure of 7000 kPa or less, a WHSV based on ethylene of from about 0.5 to about 2.0 $hr^{-1}$, and a mole ratio of benzene to ethylene of from 1:1 to 30:1.

14. A process according to claim 1, wherein the vapor phase transalkylation step (b) is carried out at a temperature of from about 260° C. to about 482° C., a pressure of from about 50 to 500 psig, a WHSV based on the total vapor feed to the reaction zone of from about 1 to about 50 $hr^{-1}$, and a mole ratio of benzene to diethylbenzene of from about 1 to 50.

15. A continuous process for preparing ethylbenzene, said process comprising the steps of:

(a) introducing benzene, benzene coboilers, and ethylene into a liquid phase alkylation reaction zone, wherein said benzene and said ethylene are reacted in the presence of an alkylation catalyst under sufficient liquid phase conditions to generate an effluent comprising ethylbenzene product, unreacted benzene, unreacted benzene coboilers, and byproducts comprising diethylbenzene and butylbenzene, said alkylation catalyst comprising an acidic solid oxide selected from the group consisting of MCM-22, MCM-49 and MCM-56;

(b) passing the effluent from said liquid phase alkylation reaction zone of step (a) to a separation zone, wherein said effluent is separated into separate streams comprising a light stream comprising unreacted benzene and benzene coboilers, (ii) an intermediate product stream, and (iii) a heavy stream comprising diethylbenzene and butylbenzene;

(c) passing said heavy stream (iii) from step (b) along with benzene and benzene coboilers to a vapor phase transalkylation reaction zone, wherein said benzene and diethylbenzene are reacted in the presence of a transalkylation catalyst under sufficient vapor phase conditions to generate an effluent comprising another ethylbenzene product and unreacted benzene, said transalkylation catalyst comprising a medium-pore size zeolite;

(d) passing the effluent from said vapor phase transalkylation reaction zone to the separation zone of step (b), wherein said effluent is separated into separate streams comprising (i) a light stream comprising unreacted benzene, (ii) an intermediate product stream, and (iii) a heavy stream comprising unreacted diethylbenzene;

(e) recycling unreacted benzene along with benzene coboilers recovered in separation steps (b) and (d) in a closed recycle loop to said alkylation reactor of step (a) and to said transalkylation reactor of step (c);

(f) introducing fresh benzene feed into said benzene recycle loop at a rate sufficient to make up for benzene converted in said alkylation zone and in said transalkylation zone, wherein said fresh benzene comprises impurities comprising benzene coboiling nonbenzene hydrocarbons having from 5 to 7 carbon atoms, said benzene coboiling hydrocarbons being at least partially converted to hydrocarbons having a different boiling point in said transalkylation zone of step (c), and butylbenzene being at least partially converted to one or more different hydrocarbons in said transalkylation zone of step (c); and (g) recovering an ethylbenzene product from the intermediate product stream of steps (b) and (d), the recovered ethylbenzene product comprising less than 200 ppm xylene, less than 100 ppm of hydrocarbons having 7 or less carbon atoms and less than 100 ppm of hydrocarbons having 9 or more carbon atoms.

16. A process according to claim 15, wherein the feed to the vapor phase transalkylation zone comprises at least 100 ppm of benzene coboilers based on the weight of benzene in the feed.

17. A process according to claim 15, wherein the feed to the vapor phase transalkylation zone comprises at least 200 ppm of benzene coboilers based on the weight of benzene in the feed.

18. A process according to claim 16, wherein said medium-pore size zeolite in step (c) is ZSM-5.

19. A process according to claim 18, wherein at least 95% of said ethylene is converted in step (a).

20. A process according to claim 19, wherein the alkylation product from step (a) comprises at least 92 wt % of ethylbenzene, less than 7 wt % of diethylbenzene and less than 1 wt % of triethylbenzene.

21. A process according to claim 20, wherein the liquid phase alkylation step (a) is carried out at a temperature of from about 150° C. to about 260° C., a pressure of 7000 kPa or less, a WHSV based on ethylene of from about 0.5 to about 2.0 $hr^{-1}$, and a mole ratio of benzene to ethylene of from 1:1 to 30:1.

22. A process according to claim 21, wherein the vapor phase transalkylation step (c) is carried out at a temperature of from about 260° C. to about 482° C., a pressure of from about 50 to 500 psig, a WHSV based on the total vapor feed to the reaction zone of from about 1 to about 50 $hr^{-1}$, and a mole ratio of benzene to diethylbenzene of from about 1 to 50.

23. A process according to claim 22, wherein fresh benzene feed is introduced immediately upstream from said separation zone of steps (b) and (d).

24. A process according to claim 23, wherein the alkylation product from step (a) comprises less than 0.5 wt % of triethylbenzene.

\* \* \* \* \*